US007119216B2

(12) United States Patent
Newman et al.

(10) Patent No.: US 7,119,216 B2
(45) Date of Patent: Oct. 10, 2006

(54) METATHESIS OF UNSATURATED FATTY ACID ESTERS OR UNSATURATED FATTY ACIDS WITH LOWER OLEFINS

(75) Inventors: Thomas H. Newman, Midland, MI (US); Cynthia L. Rand, Sanford, MI (US); Kenneth A. Burdett, Midland, MI (US); Bob R. Maughon, Midland, MI (US); Donald L. Morrison, Hurricane, WV (US); Eric P. Wasserman, Hopewell, NJ (US)

(73) Assignee: Dow Global Technologies Inc., Midland, MI (US)

( * ) Notice: Subject to any disclaimer, the term of this patent is extended or adjusted under 35 U.S.C. 154(b) by 607 days.

(21) Appl. No.: 10/469,321

(22) PCT Filed: Feb. 27, 2002

(86) PCT No.: PCT/US02/05894

§ 371 (c)(1),
(2), (4) Date: Aug. 27, 2003

(87) PCT Pub. No.: WO02/076920

PCT Pub. Date: Oct. 3, 2002

(65) Prior Publication Data
US 2005/0070750 A1 Mar. 31, 2005

Related U.S. Application Data

(63) Continuation of application No. PCT/US02/05894, filed on Feb. 27, 2002.

(60) Provisional application No. 60/278,914, filed on Mar. 26, 2001.

(51) Int. Cl.
C11C 3/00 (2006.01)
(52) U.S. Cl. .................. 554/163; 554/162; 502/155
(58) Field of Classification Search ............... 554/162, 554/163; 502/155
See application file for complete search history.

(56) References Cited

U.S. PATENT DOCUMENTS

| 4,545,941 A | 10/1985 | Rosenburg |
| 4,560,792 A | 12/1985 | Banasiak |
| 4,772,758 A | 9/1988 | Kaufhold |
| 4,943,397 A | 7/1990 | Johnson |
| 5,143,885 A | 9/1992 | Warwel et al. |
| 5,218,131 A | 6/1993 | Warwel et al. |
| 5,312,940 A | 5/1994 | Grubbs et al. |
| 5,342,985 A | 8/1994 | Herrmann et al. |
| 5,352,812 A | 10/1994 | Feldman et al. |
| 5,539,060 A | 7/1996 | Tsunogae et al. |
| 5,932,664 A | 8/1999 | Chen et al. |
| 6,060,572 A | 5/2000 | Gillis et al. |
| 6,156,692 A | 12/2000 | Nubel et al. |
| 6,197,894 B1 | 3/2001 | Sunaga et al. |
| 6,635,768 B1 | 10/2003 | Herrmann et al. |

FOREIGN PATENT DOCUMENTS

| DE | A1-281594 | 8/1990 |
| DE | 4107056 A1 | 9/1992 |
| DE | 100 41 345 | 3/2002 |
| EP | 0 084 437 A1 | 7/1983 |
| EP | 0 099 572 B2 | 2/1984 |
| EP | 0 328 230 | 8/1989 |
| JP | 56 077243 | 6/1981 |
| JP | 03 066725 A | 3/1991 |
| WO | WO 91/14665 | 10/1991 |
| WO | WO 93/20111 | 10/1993 |
| WO | WO 96/04289 | 2/1996 |
| WO | WO 97/06185 | 2/1997 |
| WO | WO 99/00397 | 1/1999 |
| WO | WO 99/22866 | 5/1999 |
| WO | WO 00/15339 | 3/2000 |
| WO | WO 00/58322 | 10/2000 |
| WO | WO 00/71554 | 11/2000 |
| WO | WO 03/093215 | 11/2003 |

OTHER PUBLICATIONS

Gessler et al. Tetrahedron Letters, vo. 41, pp. 9973-9976, 2000.*
Ahn, Yu Mi et al., "A Convenient Method for the Efficient Removal of Ruthenium Byproducts Generated During Olefin Metathesis Reactions", Organic Letters, vol. 3, pp. 1411-1413 (2001).
"An Improved Process for the Synthesis of Unsaturated Alcohols", filed in the United States of America on Oct. 9, 2003, U.S. Appl. No. 60/509,908; Applicant: Bob R. Maughon et al.
Biermann, Ursula et al., "New Syntheses with Oils and Fats as Renewable Raw Materials for the Chemical Industry", Angewandte Chemie Int. Ed., vol. 39, pp. 2207-2224 (2000).
Buchowicz, W. et al., "Catalytic Activity and Selectivity of Ru(=CHPh)Cl$_2$(PCy$_3$)$_2$ in the Metathesis of Linear Alkenes", Journal of Molecular Catalysis A: Chemical, vol. 148, pp. 97-103 (1999).

(Continued)

Primary Examiner—Deborah D. Carr
(74) Attorney, Agent, or Firm—Marie F. Zuckerman

(57) ABSTRACT

An olefin metathesis process involving contacting an unsaturated fatty acid ester or unsaturated fatty acid, such as methyloleate or oleic acid, with a lower olefin, preferably ethylene, in the presence of a metathesis catalyst so as to prepare a first product olefin, preferably, a reduced chain α-olefin, such as methyl-9-decenoate or 9-decenoic acid, respectively. The metathesis catalyst contains ruthenium or osmium and a chelating ligand, preferably, a chelating ligand containing a carbene moiety and a second donor moiety of a Group 15 or 16 element Optionally, the catalyst can be supported on a catalyst support, such as, a cross-linked polymeric resin.

25 Claims, No Drawings

OTHER PUBLICATIONS

Derwent Abstract, AN 1991-015326 (DD 281594).

Dowden, James et al., "Olefin Metathesis in Non-Degassed Solvent Using a Recyclable, Polymer Supported Alkylideneruthenium", Chemical Communications, pp. 37-38 (2001).

Gesseler, Simon et al., "Synthesis and Metathesis Reactions of a Phosphine-Free Dihydroimidazole Carbene Ruthenium Complex", Tetrahedron Letters, vol. 41, pp. 9973-9976 (2000).

Kingsbury, Jason et al., "A Recyclable Ru-Based Metathesis Catalysts", Journal of the American Chemical Society, vol. 121, pp. 791-799 (1999).

MandellI, Dalmo et al., "Ethenolysis of Esters of Vegetable Oils: Effect of $B_2O_3$ Addition to $Re_2O_7/SiO_2,Al_2O_3$-$SnBu_4$ and $CH_3ReO_3/SiO_2,Al_2O_3$ Metathesis Catalysts", Journal of the American Oil Chemical Society, vol. 73, pp. 229-232 (1996).

Maynard, Heather et al., "Purification Technique for the Removal of Ruthenium from Olefin Metathesis Reaction Products", Tetrahedron Letters, vol. 40, pp. 4137-4140 (1999).

Nubel, P.O. et al., "A Convenient Catalyst System Employing $RuCl_3$ or $RuBr_3$ for Metathesis of Acyclic Olefins", Journal of Molecular Catalysis A: Chemical, vol. 145, pp. 323-327 (1999).

Paquette, Leo et al., "A Convenient Method for Removing All Highly-Colored Byproducts Generated During Olefin Metathesis Reactions", Organic Letters, vol. 2, pp. 1259-1261 (2000).

Refvik, M.D. et al., "Ruthenium-Catalyzed Metathesis of Vegetable Oils", Journal of the American Oil Chemical Society, vol. 76, pp. 93-98 (1999).

"Stabilization of Olefin Metathesis Product Mixtures", filed in the United States Receiving Office on Sep. 26, 2003, WO Appl. No. 03/30632, Applicant: Dow Global Technologies Inc. et al.

Warwel, Siegfried et al., "Polymers and Surfactants on the Basis of Renewable Resources", Chemosphere, vo. 43, pp. 39-48 (2001).

Yao, Qingwei, "A Soluble Polymer-Bound Ruthenium Carbene Complex: A Robust and Reusable Catalyst for Ring-Closing Olefin Metathesis", Angewandte Chemie Intl. Ed., vol. 39, pp. 3896-3898 (2000); (German version:Yao, Qingwei, "Ein löslicher, polymergebundener rutheniumcarbenkomplex: ein robuster und wiederverwendbarer Katalysator für Ringschluss-Olefinmetathesen", Angewandte Chemie, vol. 112, pp. 4060-4063 (2000)).

Burdett, Kenneth A., "Renewable Monomer Feedstocks via Olefin Metathesis: Fundamental Mechanistic Studies of Methyl Oleate Ethenolysis with the First-Generation Grubbs Catalyst", Organometallics, vol. 23, pp. 2027-2047, 2004.

Burdett, Kenneth A., et al., "Stabilization of Olefin Metathesis Product Mixtures", filed in United States of America on Mar. 21, 2005, U.S. Appl. No. 10/528,472.

* cited by examiner

METATHESIS OF UNSATURATED FATTY ACID ESTERS OR UNSATURATED FATTY ACIDS WITH LOWER OLEFINS

CROSS-REFERENCE TO RELATED APPLICATIONS

This application is a continuation of International Patent Application No. PCT/US02/05894, filed Feb. 27, 2002, which claims the benefit of U.S. Provisional Patent Application Ser. No. 60/278914, filed Mar. 26, 2001.

BACKGROUND OF THE INVENTION

In one aspect, this invention pertains to an olefin metathesis process wherein an unsaturated fatty acid ester or an unsaturated fatty acid is metathesized with a lower olefin in the presence of a metathesis catalyst to prepare a first product olefin, preferably, a reduced chain α-olefin, and a second product olefin, preferably, a reduced chain ester or acid-functionalized α-olefin. In another aspect, this invention pertains to a catalyst composition containing ruthenium or osmium.

The metathesis of unsaturated fatty acid esters or unsaturated fatty acids with a lower olefin can produce valuable α-olefins of reduced chain length. As an example, methyloleate or oleic acid can be metathesized with ethylene in the presence of a metathesis catalyst to prepare methyl-9-decenoate or 9-decenoic acid, respectively, and co-product 1-decene. The aforementioned products are α-olefins of reduced chain length, as compared with the chain length of methyloleate or oleic acid. α-Olefins find utility in the manufacture of poly(olefin) polymers. Ester-functionalized α-olefins can be readily hydrolyzed to the corresponding acid-functionalized α-olefins, which find utility in thermoset polymer applications, such as thermoset urethanes and epoxies. Alternatively, acid-functionalized α-olefins can be converted into acid-functionalized α-epoxides, which also find utility, for example, in the manufacture of epoxy resins. These utilities are especially applicable when the olefin functionality and the ester or acid functionality are located at the terminal positions of the carbon chain.

It is known to metathesize long chain olefins with ethylene in the presence of a metathesis catalyst to prepare terminally unsaturated hydrocarbons of medium chain length. In certain art, as disclosed, for example, in DD-A1-281594 (East German Publication), the metathesis catalyst is taught to comprise a tungsten (VI) halide, a tetraalkyl tin compound, and an organoaluminum compound. Disadvantageously, this metathesis catalyst requires three components and performs less efficiently with ester or acid-functionalized olefins, which features adversely affect the economics of the process. More disadvantageously, the tin component of the catalyst can leach into the metathesis product stream, thereby producing contamination problems in downstream applications. Similar olefin metathesis processes are known that employ an organorhenium oxide catalyst, as disclosed, for example, in WO 91/14665. Disadvantageously, the organorhenium oxide catalyst also exhibits instability in the presence of ester or acid-functionalized olefins, and also requires a tin co-catalyst for activation. As noted above, the tin co-catalyst can disadvantageously contaminate the metathesis product stream.

Metathesis reactions have also been disclosed, as illustrated, for example, by WO 96/04289, wherein an unsaturated fatty acid ester or unsaturated fatty acid is metathesized with an olefin in the presence of an organometallic catalyst comprising ruthenium or osmium bonded to a monodentate carbene ligand and other monodentate ligands. A monodentate ligand has one binding site to the metal atom or ion, for example, the ruthenium or osmium. Disadvantageously, this catalyst characterized by its monodentate ligands exhibits low activity and a slow metathesis reaction rate.

A more robust and recyclable ruthenium-based metathesis catalyst is known, as disclosed by Jason S. Kingsbury et al. in the *Journal of the American Chemical Society*, 1999, 121, 791–799, wherein ruthenium is bound to a chelating ligand containing a carbene moiety and a second electron donor moiety, both moieties being bound to the ruthenium atom. As described in detail hereinafter, a chelating ligand has two or more binding sites to the metal atom or ion. This catalyst, which is not bound to a catalyst support, is disclosed to catalyze the metathesis of styrenyl cycloalkenyl ethers to 2-substituted chromenes; but the reference is silent with respect to use of this catalyst in the metathesis of ester or acid-functionalized long chain olefins.

In view of the above, it would be desirable to discover a metathesis process wherein an unsaturated fatty acid ester or unsaturated fatty acid is metathesized with a lower olefin for the purpose of preparing product olefins, preferably, reduced chain α-olefins and reduced chain ester or acid-functionalized α-olefins. It would be more desirable if the metathesis process employed a metathesis catalyst that was less complex and less inhibited by ester and acid functionalities, as compared with prior art metathesis catalysts. It would be more desirable, if the olefin metathesis process employed a catalyst that did not substantially leach into the metathesis product stream and did not produce significant downstream contamination problems. It would be even more desirable if the metathesis catalyst was robust and recyclable, and exhibited good activity, even when anchored to a catalyst support. An anchored catalyst, by being heterogeneous, needs no complex separation and recovery from the reaction mixture, in contrast to a homogeneous catalyst, which by being dissolved in the reaction mixture requires more complex separation and recovery schemes. Finally, it would be most advantageous, if the olefin metathesis process operated efficiently with an improved reaction rate, as compared with prior art metathesis processes. All of the above properties would render the olefin metathesis process highly desirable for converting unsaturated fatty acid esters and unsaturated fatty acids to product olefins, preferably, reduced chain α-olefins and reduced chain ester or acid-functionalized α-olefins.

SUMMARY OF THE INVENTION

This invention provides for a novel olefin metathesis process for converting two reactant olefins into two product olefins that are different from the reactant olefins. The novel metathesis process of this invention comprises contacting an unsaturated fatty acid ester or unsaturated fatty acid with a lower olefin in the presence of an olefin metathesis catalyst, the contacting being conducted under process conditions sufficient to prepare a first product olefin and an ester-functionalized or acid-functionalized second product olefin. The olefin metathesis catalyst, which is employed in the novel process of this invention, is an organometallic complex comprising ruthenium or osmium and a chelating ligand.

The novel process of this invention finds utility in the preparation of olefins, preferably α-olefins and ester or acid-functionalized α-olefins, even more preferably, reduced chain α-olefins and reduced chain ester or acid-functionalized α-olefins. As noted hereinbefore, α-olefins are valuable starting monomers in the preparation of poly(olefin) polymers. Ester-functionalized α-olefins are also useful in that they can be hydrolyzed to acid-functionalized α-olefins, which find utility in thermoset polymer applications. Moreover, acid-functionalized α-olefins can be epoxidized to form acid-functionalized α-epoxides, which are likewise useful in epoxy resin applications. In preferred embodiments of this invention, the olefin functionality and the ester or acid functionality in the metathesis products of this invention occupy terminal positions on the carbon chain, making them highly desirable materials for thermoset polymer applications.

The novel olefin metathesis process of this invention advantageously employs an olefin metathesis catalyst that performs well in the presence of ester and acid functionalities, as compared with prior art catalysts. Moreover, the metathesis catalyst employed in the process of this invention is less prone to leaching, which lessens downstream contamination problems. Additionally, the metathesis catalyst in its homogeneous form is robust, readily separated from the metathesis reaction mixture by conventional chromatographic methods, and readily recycled. Most advantageously, the unique olefin metathesis process of this invention employs a metathesis catalyst having good activity and efficiency, even when the catalyst is anchored to a catalyst support. All of the aforementioned properties of the process of this invention render this process highly desirable for converting unsaturated fatty acid esters or unsaturated fatty acids into higher valued product olefins, preferably, reduced chain α-olefins and reduced chain ester or acid-functionalized α-olefins.

In another aspect, this invention provides for a heterogeneous catalyst composition that is useful in the aforementioned metathesis process. In its broadest concept, the catalyst composition comprises an organometallic complex on a catalyst support, the organometallic complex comprising ruthenium or osmium and a chelating ligand. The chelating ligand is characterized specifically as comprising a carbene moiety and a second electron donor moiety, both moieties being bonded to the ruthenium or osmium atom.

The aforementioned heterogeneous catalyst composition of this invention exhibits good activity in processes wherein an unsaturated fatty acid ester or unsaturated fatty acid is metathesized with a lower olefin, such as ethylene, to form olefinic products, preferably, reduced chain α-olefins and reduced chain ester and acid-functionalized α-olefins. Advantageously, the catalyst of this invention requires no complex separation or recovery from the olefin metathesis reaction mixture, because the catalyst claimed herein is provided in a heterogeneous form.

DETAILED SUMMARY OF THE INVENTION

As described hereinbefore, this invention provides for a unique metathesis process of preparing useful olefins, preferably, α-olefins. This unique process comprises contacting an unsaturated fatty acid ester or unsaturated fatty acid with a lower olefin in the presence of an olefin metathesis catalyst, the contacting being conducted under process conditions sufficient to prepare a first product olefin and an ester-functionalized or acid-functionalized second product olefin. The metathesis catalyst, which is employed in the novel process of this invention, is an organometallic complex comprising ruthenium or osmium and a chelating ligand. For the purposes of this invention, the term "chelating ligand" shall mean any neutral molecule or charged ion having two or more moieties that each independently are capable of binding to the ruthenium or osmium ion.

In a preferred embodiment, the novel process of this invention comprises contacting an unsaturated fatty acid ester or an unsaturated fatty acid, either one having a $C_{8-25}$ fatty acid chain length, with a $C_{2-4}$ lower olefin in the presence of a metathesis catalyst comprising ruthenium and a chelating ligand, the contacting being conducted under conditions sufficient to prepare a reduced chain first product olefin and a reduced chain ester or acid-functionalized second product olefin. The term "reduced chain" shall refer to a carbon chain having a shorter length than the carbon chain in the fatty acid segment of the unsaturated fatty acid ester or unsaturated fatty acid.

In a more preferred embodiment, the novel process of this invention comprises contacting an unsaturated fatty acid ester or an unsaturated fatty acid, either one having a $C_{8-25}$ fatty acid chain length, with ethylene in the presence of a metathesis catalyst comprising ruthenium and a chelating ligand, the contacting being conducted under conditions sufficient to prepare a reduced chain first product α-olefin and a reduced chain ester or acid-functionalized second product α-olefin. In this more preferred embodiment, the olefin functionality and the ester or acid functionality occupy terminal positions on the carbon chain. In a most preferred embodiment related thereto, the unsaturated fatty acid ester is methyloleate; the lower olefin is ethylene; and the olefinic metathesis products include 1-decene and methyl-9-decenoate. In another most preferred embodiment related thereto, the fatty acid ester is a triglyceride, such as triolein. In another most preferred embodiment related thereto, the unsaturated fatty acid is oleic acid; the lower olefin is ethylene; and the olefinic metathesis products include 1-decene and 9-decenoic acid.

Any unsaturated fatty acid can be suitably employed in the process of this invention, provided that the unsaturated fatty acid can be metathesized in the manner disclosed herein. An unsaturated fatty acid comprises a long carbon chain containing at least one carbon-carbon double bond and terminating in a carboxylic acid group. Typically, the unsaturated fatty acid will contain greater than about 8 carbon atoms, preferably, greater than about 10 carbon atoms, and more preferably, greater than about 12 carbon atoms. Typically, the unsaturated fatty acid will contain less than about 50 carbon atoms, preferably, less than about 35 carbon atoms, and more preferably, less than about 25 carbon atoms. At least one carbon-carbon double bond is present along the carbon chain, this double bond usually occurring about the middle of the chain, but not necessarily. The carbon-carbon double bond may also occur at any other internal location along the chain. A terminal carbon-carbon double bond, at the opposite end of the carbon chain relative to the terminal carboxylic acid group, is also suitably employed, although terminal carbon-carbon double bonds occur less commonly in fatty acids. Unsaturated fatty acids containing the terminal carboxylic acid functionality and two or more carbon-carbon double bonds may also be suitably employed in the process of this invention. Since metathesis can occur at any of the carbon-carbon double bonds, a fatty acid having more than one double bond may produce a variety of metathesis products, which may then require more extensive separation efforts. Accordingly, unsaturated fatty acids containing one carbon-carbon double bond are preferred. The unsaturated fatty acid may be straight or branched and substituted along the fatty acid chain with one or more substituents, provided that the one or more substituents are substantially inert with respect to the metathesis process. Non-limiting examples of suitable substituents include alkyl moieties, preferably $C_{1-10}$ alkyl moieties, including, for example, methyl, ethyl, propyl, butyl, and the like; cycloalkyl moieties, preferably, $C_{4-8}$ cycloalkyl moieties, including for example, cyclopentyl and cyclohexyl; monocyclic aromatic moieties, preferably, $C_6$ aromatic moieties, that is, phenyl; arylalkyl moieties, preferably, $C_{7-16}$ arylalkyl moieties, including, for example, benzyl; and alkylaryl moieties, preferably, $C_{7-16}$ alkylaryl moieties, including, for example, tolyl, ethylphenyl, xylyl, and the like; as well as hydroxyl, ether, keto, aldehyde, and halide, preferably, chloro and bromo, functionalities.

Non-limiting examples of suitable unsaturated fatty acids include 3-hexenoic (hydrosorbic), trans-2-heptenoic, 2-octenoic, 2-nonenoic, cis- and trans-4-decenoic, 9-decenoic (caproleic), 10-undecenoic (undecylenic), trans-3-dodecenoic (linderic), tridecenoic, cis-9-tetradeceonic (myristoleic), pentadecenoic, cis-9-hexadecenoic (cis-9-palmitoelic), trans-9-hexadecenoic (trans-9-palmitoleic), 9-heptadecenoic, cis-6-octadecenoic (petroselinic), trans-6-octadecenoic (petroselaidic), cis-9-octadecenoic (oleic), trans-9-octadecenoic (elaidic), cis-11-octadecenoic, trans-11-octadecenoic (vaccenic), cis-5-eicosenoic, cis-9-eicosenoic (godoleic), cis-11-docosenoic (cetoleic), cis-13-docosenoic (erucic), trans-13-docosenoic (brassidic), cis-15-tetracosenoic (selacholeic), cis-17-hexacosenoic (ximenic), and cis-21-triacontenoic (lumequeic) acids, as well as 2,4-hexadienoic (sorbic), cis-9-cis-12-octadecadienoic (linoleic), cis-9-cis-12-cis-15-octadecatrienoic (linolenic), eleostearic, 12-hydroxy-cis-9-octadecenoic (ricinoleic), and like acids. Oleic acid is most preferred. Unsaturated fatty acids can be obtained commercially or synthesized by saponifying fatty acid esters, this method being known to those skilled in the art.

For the purposes of this invention, an unsaturated fatty acid ester shall be defined as the ester product of an unsaturated fatty acid and an alcohol. The alcohol can be any monohydric, dihydric, or polyhydric alcohol that is capable of condensing with the unsaturated fatty acid to form the corresponding unsaturated fatty acid ester. Typically, the alcohol contains at least one carbon atom. Typically, the alcohol contains less than about 20 carbon atoms, preferably, less than about 12 carbon atoms, and more preferably, less than about 8 carbon atoms. The carbon atoms may be arranged in a straight-chain or branched structure, and may be substituted with a variety of substituents, such as those previously disclosed hereinabove in connection with the fatty acid, including the aforementioned alkyl, cycloalkyl, monocyclic aromatic, arylalkyl, alkylaryl, hydroxyl, halogen, ether, ester, aldehyde and keto substituents. Preferably, the alcohol is a straight-chain or branched $C_{1-12}$ alkanol. A preferred alcohol is the trihydric alcohol glycerol, the fatty acid esters of which are known as "glycerides." Other preferred alcohols include methanol and ethanol.

Suitable unsaturated fatty acid esters can be obtained from vegetable and animal fats and oils, including palm, butterfat, lard and tallow fats; vegetable oils, including castor, olive, peanut, rapeseed, corn, sesame, cottonseed, soybean, sunflower, safflower, linseed, and like oils; as well as whale and fish oils. Preferably, the fatty acid ester is selected from the fatty acid esters found in plant and vegetable oils. More preferably, the fatty acid ester is derived from a $C_{8-25}$ unsaturated fatty acid segment and a $C_{1-12}$ alcohol segment. Most preferably, the fatty acid ester is methyloleate, methylricinolate, or triolein.

Besides the unsaturated fatty acid or unsaturated fatty acid ester, the metathesis process of this invention requires a lower olefin as a reactant. The term "lower olefin" shall imply an organic compound having less than about 10 carbon atoms and containing at least one carbon-carbon double bond. The lower olefin may have one carbon-carbon unsaturated bond, or alternatively, two or more carbon-carbon unsaturated bonds. Since the metathesis reaction can occur at any double bond, olefins having more than one double bond will produce more metathesis products, which will lead to more extensive downstream separation operations. Accordingly, it is preferred to employ a lower olefin having only one carbon-carbon double bond. The double bond may be, without limitation, a terminal double bond or an internal double bond. The lower olefin may also be substituted at any position along the carbon chain with one or more substituents, provided that the one or more substituents are essentially inert with respect to the metathesis process. Suitable substituents include, without limitation, alkyl, preferably, $C_{1-6}$ alkyl; cycloalkyl, preferably, $C_{3-6}$ cycloalkyl; as well as hydroxy, ether, keto, aldehyde, and halogen functionalities. Non-limiting examples of suitable lower olefins include ethylene, propylene, butene, butadiene, pentene, hexene, the various isomers thereof, as well as higher homologues thereof. Preferably, the lower olefin is a $C_{2-8}$ olefin. More preferably, the lower olefin is a $C_{2-6}$ olefin, even more preferably, a $C_{2-4}$ olefin, and most preferably, ethylene.

The unsaturated fatty acid ester or unsaturated fatty acid and the lower olefin may be fed to the process of this invention in any amounts that provide for an operable metathesis process. The actual molar ratio of lower olefin to unsaturated fatty acid ester or unsaturated fatty acid can vary depending upon the specific reactants and the specific reactor design. Generally, it is desirable to maintain amounts of lower olefin and unsaturated fatty acid ester or unsaturated fatty acid that minimize self-metathesis of the reagents, that is, metathesis between reagents of the same kind, for example, the metathesis of one unsaturated fatty acid molecule with a second unsaturated fatty acid molecule, or the metathesis of one lower olefin molecule with a second lower olefin molecule. One skilled in the art would know, without undue experimentation, how to choose the relative amounts of lower olefin and unsaturated fatty acid ester or unsaturated fatty acid so as to minimize self-metathesis. The following molar ratios are set forth as a guideline, but this invention should not be limited to the ratios disclosed herein. Typically, the molar ratio of lower olefin to unsaturated fatty acid ester or unsaturated fatty acid is greater than about 0.8/1.0, preferably, greater than about 0.9/1.0. Typically, the molar ratio of lower olefin to unsaturated fatty acid ester or unsaturated fatty acid is less than about 3.0/1.0, preferably, less than about 2.0/1.0. Depending upon the specific reagents, other molar ratios may also be suitable. With ethylene, for example, a significantly higher molar ratio can be used, because the self-metathesis of ethylene produces only ethylene again; no undesirable co-product olefins are formed. Accordingly, the molar ratio of ethylene to unsaturated fatty acid ester or unsaturated fatty acid may range from greater than about 0.8/1 to typically less than about 20/1.

Generally, the unsaturated fatty acid ester or unsaturated fatty acid is provided as a liquid at the process temperature, and it is generally preferred to be used neat, that is, without a diluent or solvent. The use of a solvent will increase recycle requirements and increase costs. Optionally, however, if desired, a solvent can be employed with the unsaturated fatty acid ester or unsaturated fatty acid. A solvent may be desirable, for instance, where a liquid lower olefin and the unsaturated fatty acid ester or unsaturated fatty acid are not entirely miscible, and both then can be solubilized in a suitable solvent. The solvent can be any thermally stable and chemically stable liquid that is also miscible with the unsaturated fatty acid ester or unsaturated fatty acid. The term "thermally stable" means that the solvent does not substantially decompose at the process temperature. The term "chemically stable" means that the solvent is substantially non-reactive with the metathesis reagents and products, and also implies that the solvent does not substantially coordinate or bond to the metathesis catalyst in a way that inhibits or impedes catalyst performance. The term "miscible" means that the solvent and unsaturated fatty acid ester or unsaturated fatty acid form a homogeneous solution essentially without phase separation. Non-limiting examples of suitable solvents include aromatic hydrocarbons, such as benzene, toluene, xylenes, and the like; chlorinated aromatic hydrocarbons, preferably chlorinated benzenes, such as chlorobenzene and dichlorobenzene; alkanes, such as pentane, hexane, cyclohexane, and the like; and chlorinated alkanes, such as methylene chloride and chloroform. If a solvent is used, then any amount can be employed, provided that the metathesis process proceeds as desired. Generally, the concentration of the unsaturated fatty acid ester or unsaturated fatty acid in the solvent is greater than about 0.05 M, preferably, greater than about 0.5 M. Generally, the concentration of unsaturated fatty acid ester or unsaturated fatty acid in the solvent is less than about the saturation concentration, preferably, less than about 5.0 M.

When the lower olefin and unsaturated fatty acid ester or unsaturated fatty acid are both provided in liquid phase, then the metathesis process is preferably conducted under an inert atmosphere, so as to minimize interference by oxygen. The inert atmosphere may comprise any gas or gaseous mixture that is essentially inert with respect to the metathesis process. Suitable inert atmospheres include, without limitation, helium, neon, argon, nitrogen, and mixtures thereof.

If the lower olefin is provided to the metathesis process as a gas, as it will be in preferred embodiments, then the lower olefin may be fed to the reactor as an essentially pure gas or, optionally, diluted with a gaseous diluent. As the gaseous diluent, any essentially inert gas may be used, suitable examples of which include, without limitation, helium, neon, argon, nitrogen, and mixtures thereof. The concentration of lower olefin in the gaseous diluent may be any concentration which provides for an operable metathesis process. Suitable concentrations typically are greater than about 5 mole percent lower olefin, and preferably, greater than about 10 mole percent lower olefin, based on the total moles of lower olefin and gaseous diluent. Suitable concentrations are typically less than about 90 mole percent lower olefin, based on the total moles of lower olefin and gaseous diluent; however, concentrations other than the aforementioned concentrations also may be found to be suitable.

As a further option, a stabilizing ligand may be added to the metathesis reaction mixture. The stabilizing ligand may be any molecule or ion that promotes catalyst stability in the metathesis process, as measured, for example, by increased activity or extended catalyst lifetime. Non-limiting examples of stabilizing ligands include tri(alkyl)phosphines, such as tricyclohexylphosphine, tricyclopentylphosphine, and tributylphosphine; tri(aryl)phosphines, such as tri(phenyl)phosphine, tri(methylphenyl)phosphine (ortho, meta, and para substituted isomers), and tri(p-fluorophenyl)phosphine; diarylalkylphosphines, for example, diphenylcyclohexylphosphine; dialkylarylphosphines, such as dicyclohexylphenylphosphine; ethers, such as anisole; pyridines, such as 2,6-dimethylpyridine, 2-t-butylpyridine, 2,6-difluoropyridine, and 2-methylpyridine; phosphine oxides, such as triphenylphosphine oxide; as well as phosphinites, phosphonites, phorphoramidites, and mixtures of any of the aforementioned ligands. Preferably, the stabilizing ligand is a tri(alkyl)phosphine, more preferably, tri(cyclohexyl)phosphine. Any quantity of stabilizing ligand may be employed, provided that the process proceeds to the desired metathesis products. The quantity of stabilizing ligand can vary, however, depending upon the specific catalyst employed and its specific ligand components. Typically, the molar ratio of stabilizing ligand to catalyst is greater than about 0.05/1, and preferably, greater than about 0.5/1. Typically, the molar ratio of stabilizing ligand to catalyst is less than about 2.0/1, and preferably, less than about 1.5/1.

In its broadest concept, the metathesis catalyst comprises ruthenium or osmium and a chelating ligand. Ruthenium is preferred. As noted hereinbefore, the term "chelating ligand" refers to any molecule or ion that has a plurality of moieties (two or more groups), each of which is capable of binding to the ruthenium or osmium atom. Preferably, the metathesis catalyst is represented by the following formula:

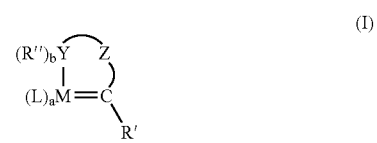

wherein M is Ru or Os; each L is independently selected from neutral and anionic ligands in any combination that balances the bonding and charge requirements of M; a is an integer, preferably from 1 to about 4, which represents the total number of ligands L; R' is selected from hydrogen, straight-chain or branched alkyl, cycloalkyl, aryl, and substituted aryl radicals; Y is an electron donor group, otherwise known as a Lewis base, of an element from Group 15 or 16 of the Periodic Table, as referenced by the IUPAC in *Nomenclature of Inorganic Chemistry: Recommendations 1990*, G. J. Leigh, Editor, Blackwell Scientific Publications, 1990; Y being more preferably O, S, N, or P; each R" is independently selected from hydrogen, alkyl, cycloalkyl, aryl, and substituted aryl radicals sufficient to satisfy the valency of Y, preferably such that Y is formally neutral; b is an integer, preferably 0 to about 2, representing the total number of R" radicals; and Z is an organic diradical that is bonded to both Y and the carbene carbon (C) so as to form a bidentate ligand, which ligand in connection with the M atom forms a ring of from about 4 to about 8 atoms. A bidentate ligand has two binding sites to the metal atom. More preferably, each L is independently selected from the group consisting of halides, most preferably, fluoride, chloride, bromide, and iodide; cyanide, thiocyanate, phosphines of the formula $PR_3$, amines of the formula $NR_3$, water and ethers of the formula $OR_2$, thioethers of the formula $SR_2$, and ligands having the formulas II and III hereinafter:

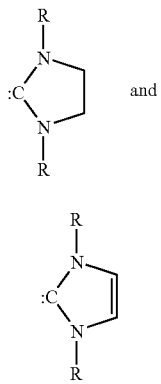

(II)

(III)

wherein each R in any of the aforementioned formulas is independently selected from the group consisting of hydrogen, alkyl, preferably, $C_{1-15}$ alkyl; cycloalkyl, preferably, $C_{3-8}$ cycloalkyl; aryl, preferably, $C_{6-15}$ aryl, and substituted aryl, preferably $C_{6-15}$ substituted aryl, radicals. Mixtures of any of the aforementioned ligands L may be employed in any given species of formula I. More preferably, R' is selected from the group consisting of hydrogen, $C_{1-15}$ alkyl, $C_{3-8}$ cycloalkyl, and $C_{6-15}$ aryl radicals. More preferably, each R" is independently selected from the group consisting of $C_{1-15}$ alkyl, $C_{3-8}$ cycloalkyl, and $C_{6-15}$ aryl radicals. Preferably, Z is selected from the following diradicals: ethylene (IV), vinylene (V), phenylene (VI), substituted vinylenes (VII), substituted phenylenes (VIII), naphthylene (IX), substituted naphthylenes (X), piperazindiyl (XI), piperidiyl (XII):

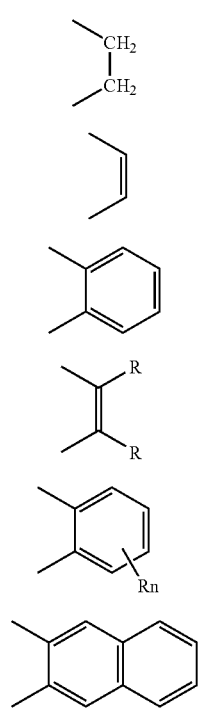

(IV)

(V)

(VI)

(VII)

(VIII)

(IX)

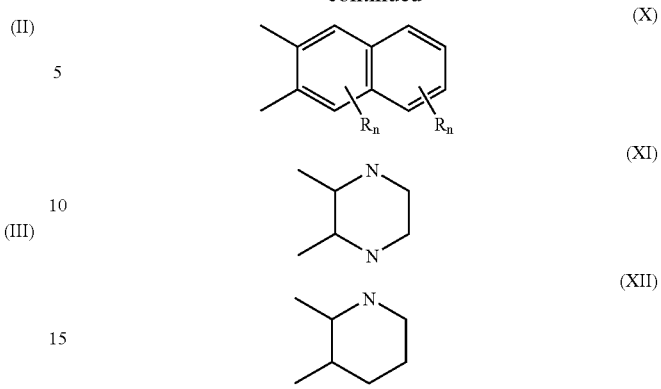

(X)

(XI)

(XII)

wherein each R may be, as noted above, selected from hydrogen, alkyl, preferably, $C_{1-15}$ alkyl; cycloalkyl, preferably, $C_{3-8}$ cycloalkyl; and aryl, Preferably, $C_{6-15}$ aryl, radicals; and wherein each n is an integer from 1 to about 4.

Even more preferably, each L is independently selected from tri(alkyl)phosphines, chloride, and bromide; Y is an oxygen atom; R" is an alkyl radical; and Z is a phenylene. Most preferably, the metathesis catalyst is {dihalo[2(1-methylethoxy-α-O)phenyl]methylene-α-C](tricyclohexylphosphine)ruthenium}, represented by formula XIII:

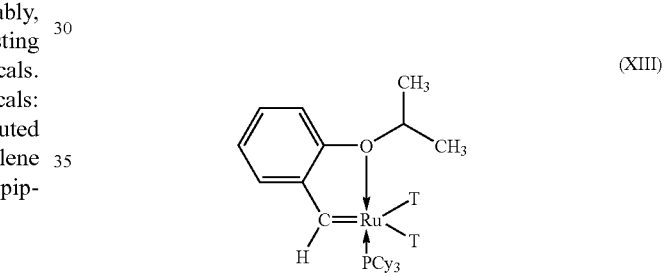

(XIII)

wherein each T is independently selected from Cl and Br, and $PCy_3$ is tricyclohexylphosphine.

Methods for synthesizing ruthenium and osmium carbene complexes are known to those skilled in the art. General methods can be found in (1) *Transition Metals in the Synthesis of Complex Organic Molecules* by L. S. Hegedus, University Science Books, 1994 and (2) *Angew. Chem. Int. Ed. Eng.* 1995, 34, 2039–2041, by P. Schwab, M. B. France, J. W. Ziller and R. H. Grubbs. The synthesis of the aforementioned ruthenium carbene complex (XIII) is disclosed by Jason S. Kingsbury et al., *Journal of the American Chemical Society*, 1999, 121, 791–799. A typical preparation of XIII involves, for example, treating a solution containing a reactant complex of ruthenium, such as dichloro-bis-(triphenylphosphine)ruthenium (II), with an excess of aryldiazomethane, such as α-alkoxyphenyldiazomethane, more preferably, α-isopropoxyphenyldiazomethane, to yield the corresponding monophosphine ruthenium carbene complex, with addition thereafter, if desired, of a more preferred phosphine ligand, such as tricyclohexylphosphine. The reaction conditions typically include mixing the ruthenium reactant complex and the aryldiazomethane in an organic solvent, such as methylene dichloride, pentane, or a mixture thereof, for several minutes (about 5–30 minutes typically) at a temperature typically less than about ambient (taken as 22° C.), and preferably, as low as about −78° C. The diazomethane is used in a molar excess ranging generally from greater than about 1:1 to less than about 3:1, as compared with the reactant ruthenium complex. Afterwards, the phosphine ligand of interest is added in excess, from greater than about 1:1 to less than about 3:1, relative to the starting ruthenium complex; and the mixture is allowed to warm to room temperature. Typically, removal of the volatiles affords the ruthenium carbene catalyst, which may optionally be purified by passage through a column of silica gel, as described in the art. Other general methods of preparing ruthenium and osmium organometallic complexes having the ligands, preferably bidentate ligands, described herein can also be found in the prior art.

In another embodiment, the catalyst employed in the process of this invention may be bound to or deposited on a solid catalyst support. The solid catalyst support will render the catalyst heterogeneous, which will simplify catalyst recovery. In addition, the catalyst support may increase catalyst strength and attrition resistance. Suitable catalyst supports include, without limitation, silicas, aluminas, silica-aluminas, aluminosilicates, including zeolites and other crystalline porous aluminosilicates; as well as titanias, zirconia, magnesium oxide, carbon, and cross-linked, reticular polymeric resins, such as functionalized cross-linked polystyrenes, e.g., chloromethyl-functionalized cross-linked polystyrenes. The catalyst may be deposited onto the support by any method known to those skilled in the art, including, for example, impregnation, ion-exchange, deposition-precipitation, and vapor deposition. Alternatively, the catalyst may be chemically bound to the support via one or more covalent chemical bonds, a preferred example of which is shown hereinafter in Formula XIV for the most preferred ruthenium catalyst bonded to cross-linked polystyrene (X-PS):

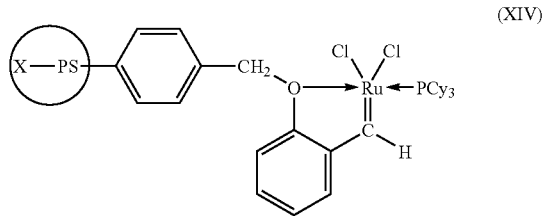

(XIV)

wherein $PCy_3$ is tricyclohexylphosphine, and wherein one or both chloride ligands may optionally be replaced by bromide. Methods for chemically binding organometallic complexes to polymeric supports are well known in the art, as disclosed, for example, by Stephen B. Roscoe, et al., *Journal of Polymer Science: Part A: Polym. Chem.*, 2000, 38, 2979–2992, and by Mahmood Ahmed, et al., *Tetrahedron Letters*, 1999, 40, 8657–8662.

If a catalyst support is used, the catalyst may be loaded onto the catalyst support in any amount, provided that the metathesis process of this invention proceeds to the desired metathesis products. Generally, the catalyst is loaded onto the support in an amount that is greater than about 0.01 weight percent ruthenium or osmium, and preferably, greater than about 0.05 weight percent ruthenium or osmium, based on the total weight of the catalyst plus support. Generally, the catalyst is loaded onto the support in an amount that is less than about 20 weight percent ruthenium or osmium, and preferably, less than about 10 weight percent ruthenium or osmium, based on the total weight of the catalyst and support.

The metathesis process of this invention can be conducted in any reactor suitably designed for such processes, including batch reactors, continuous stirred tank reactors, continuous flow fixed bed reactors, slurry reactors, fluidized bed reactors, and catalytic distillation reactors. The form of the catalyst may influence the choice of reactor. For example, if the catalyst is provided in homogeneous form, then a batch reactor may be preferable. If the catalyst is provided in heterogeneous form, then a continuous flow fixed bed reactor, fluidized bed reactor, or catalytic distillation reactor may be preferable. Typically, the unsaturated fatty acid ester or unsaturated fatty acid is provided in a liquid phase, preferably neat; while the lower olefin is provided as a gas that is dissolved in the liquid phase.

The metathesis process of this invention can be conducted under any process conditions, for example, temperature, pressure, and liquid and gas flow rates, sufficient to produce the desired metathesis products. Typically, the process temperature is greater than about 0° C., preferably, greater than about 20° C. Typically, the process temperature is less than about 150° C., preferably, less than about 120° C., and more preferably, less than about 90° C. Typically, with the use of a gaseous olefin, the olefin pressure is greater than about 5 psig (34.5 kPa), preferably, greater than about 10 psig (68.9 kPa), and more preferably, greater than about 45 psig (310 kPa). Typically, the olefin pressure is less than about 1,000 psig (6,895 kPa), preferably, less than about 750 psig (3,447 kPa), and more preferably, less than about 500 psig (2,758 kPa). When a diluent is used with the gaseous olefin, the aforementioned pressure ranges may also be suitably employed as the total pressure of olefin and diluent. Likewise, when a liquid olefin is employed and the process is conducted under an inert gaseous atmosphere, then the aforementioned pressure ranges may be suitably employed for the inert gas pressure.

The quantity of metathesis catalyst that is employed in the process of this invention is any quantity that provides for an operable metathesis reaction. If the process is conducted in a batch reactor, the ratio of moles of unsaturated fatty acid ester or unsaturated fatty acid to moles of metathesis catalyst is typically greater than about 10:1, preferably, greater than about 50:1, and more preferably, greater than about 100:1. If the process is conducted in a batch reactor, the molar ratio of unsaturated fatty acid ester or unsaturated fatty acid to metathesis catalyst is typically less than about 10,000,000:1, preferably, less than about 1,000,000:1, and more preferably, less than about 500,000:1. The contacting time of the reagents and catalyst in a batch reactor can be any duration, provided that the desired olefin metathesis products are obtained. Generally, the contacting time in a batch reactor is greater than about 5 minutes, and preferably, greater than about 10 minutes. Generally, the contacting time in a batch reactor is less than about 25 hours, preferably, less than about 15 hours, and more preferably, less than about 10 hours.

If the process is conducted in a continuous flow reactor, then the weight hourly space velocity, given in units of grams unsaturated fatty acid ester or grams unsaturated fatty acid per gram catalyst per hour ($h^{-1}$), will determine the relative quantities of unsaturated fatty acid ester or unsaturated fatty acid to catalyst employed, as well as the residence time in the reactor of the unsaturated starting compound. In a flow reactor, the weight hourly space velocity of the unsaturated fatty acid ester or unsaturated fatty acid is typically greater than about 0.04 g unsaturated fatty acid ester or unsaturated fatty acid per g catalyst per hour ($h^{-1}$), and preferably, greater than about 0.1 $h^{-1}$. In a flow reactor, the weight hourly space velocity of the unsaturated fatty acid ester or unsaturated fatty acid is typically less than about 100 h$^{-1}$, and preferably, less than about 20 h$^{-1}$. The flow of the lower olefin, which may be introduced into the reactor as a gas or a liquid stream, may be adjusted so as to produce the desired ratio of olefin to unsaturated fatty acid ester or unsaturated fatty acid, as the case may be, this ratio having been described hereinabove.

When the process of this invention is conducted as described hereinabove, then the lower olefin and unsaturated fatty acid ester or unsaturated fatty acid are co-metathesized to form first and second product olefins, preferably, a reduced chain first product α-olefin and a second product reduced chain terminal ester or acid-functionalized α-olefin. As a more preferred example, the metathesis of methyloleate with ethylene will yield co-metathesis products of 1-decene and methyl-9-decenoate. Both products are α-olefins; the decenoate also terminates in an ester moiety at the opposite end of the chain from the carbon-carbon double bond. In addition to the desired products, the methyloleate may self-metathesize to produce small amounts of 9-octadecene, a less desirable product, and dimethyloctadec-9-enoate, $CH_3OOC(CH_2)_7CH=CH(CH_2)_7COOCH_3$, a second less desirable product.

In the process of this invention, the conversion of unsaturated fatty acid ester or unsaturated fatty acid can vary widely depending upon the specific reagent olefins, the specific catalyst, and specific process conditions employed. For the purpose of this invention, "conversion" is defined as the mole percentage of unsaturated fatty acid ester or unsaturated fatty acid that is converted or reacted to products. Typically, the conversion of unsaturated fatty acid ester or unsaturated fatty acid is greater than about 50 mole percent, preferably, greater than about 60 mole percent, and more preferably, greater than about 70 mole percent.

In the process of this invention, the yields of first product olefin and ester or acid-functionalized second product olefin can also vary depending upon the specific reagent olefins, catalyst, and process conditions employed. For the purposes of this invention "yield" will be defined as the mole percentage of product olefin formed relative to the initial moles of unsaturated fatty acid ester or unsaturated fatty acid in the feed. Typically, the yield of α-olefin Will be greater than about 35 mole percent, preferably, greater than about 50 mole percent. Typically, the yield of ester or acid-functionalized α-olefin will be greater than about 35 mole percent, preferably, greater than about 50 mole percent.

The Glossary set forth hereinbelow is provided as a supplement to various aspects of the aforementioned disclosure.

Glossary

The term "ligand" shall refer to a molecule, ion, or atom that is bonded or attached to a central atom, typically a metal atom, in a complex or coordination compound. Ligands may be either neutral, positively, or negatively charged. Ligands may be a single atom, a single ion, or an inorganic or organic molecule, e.g., halide or trialkylphosphine.

The term "complex" or "coordination compound" shall refer to a compound formed by the union of a metal atom or ion, such as a central transition metal atom or ion, with a ligand or complexing agent, particularly non-metallic varieties thereof. The metal ion typically acts as a Lewis acid (electron acceptor). The ligand, typically a Lewis base (electron donor), has one or more electrons, typically electron pairs, that can be either donated or shared with the metal ion.

The term "chelating ligand" shall refer to a ligand that possesses a plurality of sites or functionalities (two or more) that are capable of bonding to the central atom or ion.

The term "bidentate ligand" shall refer to a ligand that possesses two sites or functionalities that are capable of bonding to the central atom or ion. A "tridentate ligand" shall possess three sites or functionalities that are capable of bonding to the central atom or ion.

Pressure in units of pounds per square inch gauge (psig) is converted to pressure in units of kiloPascals (kPa) as follows: Multiply psig by 6.895. (Example: 50 psig× 6.895=345 kPa).

The following examples are provided as illustrations of the process of this invention, but should not be construed as limiting the invention in any manner. In light of the disclosure herein, those of skill in the art will recognize modifications in the reagents, catalyst, and metathesis process conditions that fall within the scope of this invention.

EXAMPLE 1

A ruthenium complex with a chelating ligand was prepared following the literature procedure of J. S. Kingsbury et al., *Journal of the American Chemical Society*, 121 (1999), 791. Specifically, the complex prepared was {dichloro[2(1-methylethoxy-α-O)phenyl]methylene-α-C] (tricyclohexyl-phosphine)ruthenium} having Formula XIII, wherein the two halo moieties were chloride. The chelating ligand contained one carbene moiety and an isopropoxy moiety, both of which were capable of bonding to the Ru atom.

In a dry box, a solution was prepared of the ruthenium complex (0.01 M) in toluene. Methyloleate (purchased from Aldrich Company) was degassed with nitrogen and passed through a column of activated alumina prior to use. In a dry box, a reactor was charged with the following reagents: methyloleate (3.50 g, purified as described above), tetradecane (0.50 g, used as an internal standard for gas chromatography analysis), and the catalyst solution (265 microliters, 0.01 M solution). The molar ratio of methyloleate to ruthenium was 4,500/1. The reactor was sealed, removed from the dry box, and attached to an ethylene manifold (ethylene, 99.8 percent purity, polymer grade). The metathesis reaction was conducted at 60 psig ethylene (413.7 kPa) and 30° C. Aliquot samples were removed from the reactor and analyzed by gas chromatography with the results shown in Table 1.

TABLE 1

Methathesis of Methyloleate with Ethylene
Using Chelated Ruthenium Catalyst[a]

|   | Time (h) | % Yield 1-Decene | % Yield methyl-9-decenoate |
|---|---|---|---|
| E-1 | 1 | 54 | 54 |
| " | 3 | 57 | 57 |
| CE-1 | 1 | 38 | 37 |
| " | 3 | 48 | 47 |

[a]Process conditions: methyl oleate/catalyst molar ratio = 4,500:1; 30° C.; 60 psig (413.7 kPa)

From Table 1 it is seen that 1-decene, an α-olefin, and methyl-9-decenoate, an ester-terminated α-olefin, were produced in yields of 54 percent in only 1 h of reaction time.

Comparative Experiment 1

Example 1 was repeated, with the exception that [dichloro (phenylmethylene)bis(tricyclohexylphosphine)ruthenium] of formula (XV) was used in place of the chelated ruthenium catalyst of Example 1. (PCy$_3$ in Formula XV represents tricyclohexylphosphine.) The catalyst was purchased from Strem Chemicals, Inc. Note that the ligands in the comparative catalyst were all monodentate ligands.

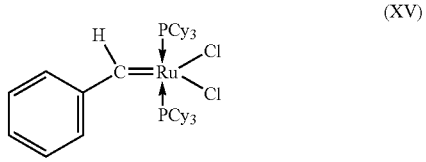

(XV)

Results are set forth in Table 1, where it is seen that the comparative catalyst achieved a 37 percent yield of 1-decene and a 38 percent yield of methyl-9-decenoate in 1 h and a 48 percent yield of 1-decene and a 47 percent yield of methyl-9-decenoate in 3 h. When Example 1 was compared with Comparative Experiment 1, it was seen that the process of this invention, which employed a catalyst with a chelating ligand, proceeded to a higher yield of α-olefin products at a faster reaction rate, as compared with the comparative process, wherein a catalyst having monodentate ligands was employed.

EXAMPLE 2

A polystyrene-supported chelated ruthenium complex was prepared as follows. First, a cross-linked polystyrene was functionalized. A solution of 2,3-dihydrobenzofuran (1.44 g, 11.9 mmol) in approximately 30 mL of degassed, anhydrous dimethylsulfoxide was added via cannula to sodium amide (0.466 g, 11.9 mmol) at room temperature. The resulting pale yellow solution was stirred at room temperature for 4 hours. Then, the solution was added via cannula to a cross-linked polystyrene resin (Merrifield resin, 3.0 g, 1.95 mmol Cl/g, 1% crosslinked) swollen with 50 ml of degassed, anhydrous tetrahydrofuran. The resulting mixture was stirred overnight at room temperature. The mixture was then heated at 55° C. for 3 hours. Afterwards, the mixture was cooled to room temperature, and methanol (100 mL) was added. A polymer product was isolated by filtration, washed with tetrahydrofuran, water, and again with tetrahydrofuran, and then dried under vacuum overnight, yielding the functionalized, cross-linked polystyrene.

In a dry box, a solution of the ruthenium catalyst of Comparative Experiment 1, (0.16 g, 0.195 mmol in 4 mL of methylene chloride) was added to the functionalized crosslinked polystyrene (1.0 g) swollen in 40 ml of methylene chloride. Copper (I) chloride (19 mg) was added and the resulting mixture stirred for 2 hours at room temperature. The brown polymer product was isolated by filtration; there was no color in the filtrate. The polymer was washed with methylene chloride and dried under vacuum. The sample was analyzed via neutron activation and found to contain 1.33 weight percent ruthenium. The catalyst composition had the structure of Formula XIV; note that the composition contained a bidentate ligand having a carbene moiety and a Group 16 element.

The supported ruthenium catalyst was evaluated in the metathesis of methyloleate with ethylene, in the manner described in Example 1, with the exception that the polymer-supported catalyst was weighed into the reactor first and swollen with 1 g of anhydrous, degassed toluene. A quantity of polymer-supported catalyst was used that correlated to a mole ratio of methyloleate to ruthenium of 4,500/1. Ethylene pressure was 60 psig (414 kPa); temperature was 50° C. Under these conditions, the supported catalyst achieved at 20 h a 1-decene yield of 44.6 percent, and a methyl-9-decenoate yield of 43.4 percent. The results indicate that the chelated ruthenium complex can be supported on a catalyst support and used as a heterogeneous catalyst in the olefin metathesis process of this invention.

EXAMPLE 3

The process of Example 1 was repeated, with the exception that tricyclohexylphosphine (1 equivalent per equivalent of chelating catalyst) was added as a stabilizing ligand to the process. Under the same process conditions as Example 1, the catalyst achieved a 53 percent yield of 1-decene at 2 h, a 57 percent yield at 5 h, and a 66 percent yield at 23 h. A second olefin product, methyl-9-decenoate, was obtained with similar results.

EXAMPLE 4

This example shows the effect of ethylene pressure on the metathesis of methyloleate using the chelated ruthenium catalyst of Example 1. The example was conducted in a manner similar to Example 1, with the results shown in Table 2.

TABLE 2

Metathesis of Methyloleate with Ethylene Using Chelated Ruthenium Catalyst: Effect of Pressure

| Pressure psig (kPa) | Time (hrs) | % Conv Methyl-Oleate | % Yield 1-Decene | % Yield Methyl-9-decenoate | % Yield 9-Octa-decene |
|---|---|---|---|---|---|
| 60 (414) | 1 | 65.2 | 54.5 | 53.9 | 3.2 |
| 60 (414) | 3 | 70.8 | 57.6 | 56.9 | 3.7 |
| 200 (1,379) | 1 | 55.6 | 56.2 | 54.9 | 0.7 |
| 200 (1,379) | 4 | 57.5 | 58.1 | 56.8 | 0.7 |
| 450 (3,103) | 4 | 53.0 | 54.8 | 53.5 | 0.4 |

It was found that the yields of 1-decene and methyl-9-decenoate were substantially unchanged as a function of pressure, over the pressure range tested. Notably, however, with increasing pressure there was a decrease in conversion, but advantageously a significant decrease in 9-octadecene, an undesirable self-metathesis product. This decrease in 9-octadecene translates into an improvement in selectivity, that is, preservation of raw material and increased productivity to desired products.

What is claimed is:

1. An olefin metathesis process comprising contacting an unsaturated fatty acid ester or unsaturated fatty acid with a lower olefin in the presence of a metathesis catalyst under process conditions sufficient to prepare a first olefin product and an ester-functionalized or acid-functionalized second olefin product, the catalyst comprising ruthenium or osmium and a chelating ligand.

2. The process of claim 1 wherein the unsaturated fatty acid contains from greater than about 8 to less than about 50 carbon atoms and contains at least one carbon-carbon double bond.

3. The process of claim 2 wherein the unsaturated fatty acid is oleic acid.

4. The process of claim 1 wherein the unsaturated fatty acid ester is derived from a $C_{8-50}$ unsaturated fatty acid segment having at least one carbon-carbon double bond and from a $C_{1-20}$ alcohol segment.

5. The process of claim 4 wherein the unsaturated fatty acid ester is methyloleate or a glyceride.

6. The process of claim 1 wherein the lower olefin is a $C_{2-8}$ olefin.

7. The process of claim 6 wherein the lower olefin is ethylene, and wherein, optionally, the molar ratio of ethylene to unsaturated fatty acid ester or unsaturated fatty acid is greater than about 0.8/1 and less than about 20/1.

8. The process of claim 1 wherein the metathesis catalyst is represented by the formula:

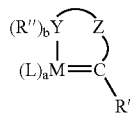

wherein M is Ru or Os; each L is independently selected from neutral and anionic ligands in a combination that balances the bonding and charge requirements of M; a is an integer from 1 to about 4; R' is selected from hydrogen, alkyl, cycloalkyl, aryl, and substituted aryl radicals; Y is an element from Group 15 or 16 of the Periodic Table; each R" is independently selected from hydrogen, alkyl, cycloalkyl, aryl, and substituted aryl radicals sufficient to satisfy the valency of Y; b is an integer from 0 to about 2; and Z is an organic diradical that is bonded to both Y and the carbene carbon (C) so as to form a bidentate ligand, which ligand in connection with the M atom forms a ring of from about 4 to about 8 atoms.

9. The process of claim 8 wherein each L is independently selected from the group consisting of fluoride, chloride, bromide, iodide, cyanide, thiocyanate, phosphines of the formula $PR_3$, amines of the formula $NR_3$, water and ethers of the formula $OR_2$, thioethers of the formula $SR_2$, and ligands having the formulas hereinafter:

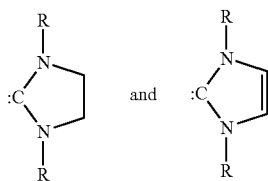

wherein each R in any of the aforementioned formulas is independently selected from the group consisting of hydrogen, $C_{1-15}$ alkyl, $C_{3-8}$ cycloalkyl, $C_{6-15}$ aryl, and $C_{6-15}$ substituted aryl radicals.

10. The process of claim 8 wherein Z is selected from the group consisting of: ethylene (IV), vinylene (V), phenylene (VI), substituted vinylenes (VII), substituted phenylenes (VIII), naphthylene (IX), substituted naphthylenes (X), piperazindiyl (XI), piperidiyl (XII), as shown in the formulas below:

(IV)

(V)

(VI)

(VII)

(VIII)

(IX)

(X)

(XI)

(XII)

wherein each R is independently selected from hydrogen, $C_{1-15}$ alkyl, $C_{3-8}$ cycloalkyl, and $C_{6-15}$ aryl radicals; and wherein each n is an integer from 1 to about 4.

11. The process of claim 8 wherein M is ruthenium, and optionally, wherein L is selected from halides and trialkylphosphines, and Z is phenylene.

12. The process of claim 1 wherein the catalyst is {dihalo [2(1-methylethoxy-α-O)phenyl]methylene-α-C](tricyclohexylphosphine)-ruthenium} having the formula:

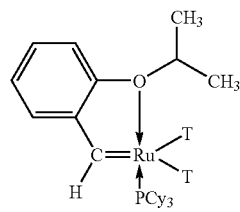

wherein each T is independently selected from Cl and Br, and $PCy_3$ is tricyclohexylphosphine.

13. The process of claim 1 wherein the catalyst is supported on a catalyst support selected from the group consisting of silicas, aluminas, silica-aluminas, aluminosilicates, titanias, zirconia, magnesium oxide, carbon, and cross-linked reticular polymeric resins, and optionally, wherein the catalyst is loaded onto the support in an amount that is greater than about 0.01 weight percent and less than about 20 weight percent catalytic metal, based on the total weight of the catalyst and support.

14. The process of claim 1 wherein a stabilizing ligand is added to the process selected from the group consisting of trialkylphosphines, triarylphosphines, diarylalkylphosphines, aryldialkylphosphines, ethers, pyridines, phosphine oxides, phosphinites, phosphonites, phosphoramidites, and mixtures thereof, and wherein optionally, the molar ratio of stabilizing ligand to catalyst is greater than about 0.0 5/1 and less than about 2.0/1.

15. The process of claim 1 wherein the process is conducted in a reactor selected from batch, fixed-bed continuous flow, slurry, fluidized bed, continuous stirred tank, and catalytic distillation reactors.

16. The process of claim 1 wherein the process is conducted at a temperature greater than about 0° C. and less than about 150° C. and at a total pressure greater than about 5 psig (34.5 kPa) and less than about 1,000 psig (6,895 kPa).

17. The process of claim 1 wherein the process is conducted in a batch reactor at a molar ratio of unsaturated fatty acid ester or unsaturated fatty acid to catalyst of greater than about 10:1 and less than about 10,000,000:1; or wherein the process is conducted in a continuous or intermittent flow reactor at a weight hourly space velocity of unsaturated fatty acid ester or unsaturated fatty acid of greater than about 0.04 h$^{-1}$ to less than about 100 h$^{-1}$.

18. The process of claim 1 wherein the first product olefin is a reduced chain α-olefin and the second product olefin is a reduced chain ester or acid-functionalized α-olefin, wherein the ester or acid functionality is in a terminal position; and optionally wherein the α-olefin is produced in a yield greater than about 35 mole percent, and the ester or acid-functionalized α-olefin is produced in a yield greater than about 35 mole percent.

19. An olefin metathesis process comprising contacting an unsaturated fatty acid ester or unsaturated fatty acid, the unsaturated reactant having an unsaturated fatty acid segment of greater than about 8 and less than about 25 carbon atoms, with ethylene in the presence of a metathesis catalyst under process conditions sufficient to prepare a reduced-chain α-olefin and a reduced-chain terminal ester or acid-functionalized α-olefin, the metathesis catalyst comprising ruthenium and a chelating ligand, optionally supported on a catalyst support.

20. The process of claim 19 wherein the fatty acid ester is an ester of glycerol.

21. The process of claim 19 wherein the fatty acid ester is methyloleate or the fatty acid is oleic acid, and the metathesis products are 1-decene and either methyl-9-decenoate or 9-decenoic acid, respectively.

22. The process of claim 19 wherein the chelating ligand contains a carbene moiety and a second donor moiety of a Group 15 or 16 element of the Periodic Table.

23. The process of claim 19 wherein the catalyst is {dihalo[2(1-methylethoxy-α-O)phenyl]methylene-α-C](tricyclohexylphosphine)-ruthenium}, represented by formula:

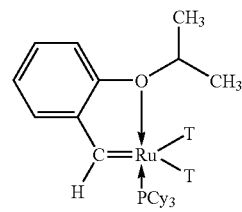

wherein each T is independently selected from Cl and Br, and PCy$_3$ is tricyclohexylphosphine; or the catalyst is a supported variation thereof.

24. A heterogeneous catalyst composition comprising an organometallic complex and a catalyst support, wherein the organometallic complex comprises a ruthenium or osmium atom and a chelating ligand, the chelating ligand having a carbene moiety and an electron donor moiety of an element from Group 15 or Group 16 of the Periodic Table, both the carbene moiety and the electron donor moiety being bonded to the ruthenium or osmium atom; and further characterized in that when the catalyst support is a cross-linked polystyrene support, the organometallic complex is bonded to the support through a benzyl linkage.

25. The heterogeneous catalyst composition of claim 24 having the formula:

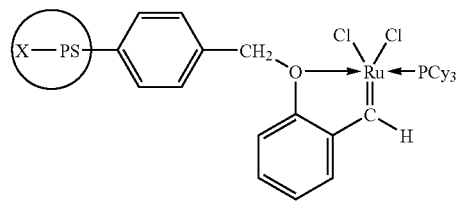

wherein PCy$_3$ is tricyclohexylphosphine, and X-PS is a cross-linked polystyrene resin, and wherein optionally, one or both chloride ions may be replaced by bromide.

* * * * *

UNITED STATES PATENT AND TRADEMARK OFFICE
CERTIFICATE OF CORRECTION

| | | |
|---|---|---|
| PATENT NO. | : 7,119,216 B2 | Page 1 of 1 |
| APPLICATION NO. | : 10/469321 | |
| DATED | : October 10, 2006 | |
| INVENTOR(S) | : Thomas H. Newman et al. | |

It is certified that error appears in the above-identified patent and that said Letters Patent is hereby corrected as shown below:

In the specification, page one is amended by adding a paragraph before the Background of Invention paragraph on Col. 1, line 12, to read as follows:

This invention was made with U.S. Government support under contract DE-FC36-01ID14213 awarded by the Department of Energy. The U.S. Government has certain rights in this invention.

Signed and Sealed this
Twenty-seventh Day of November, 2012

David J. Kappos
*Director of the United States Patent and Trademark Office*